United States Patent [19]

Kiff et al.

[11] 4,421,939
[45] Dec. 20, 1983

[54] PRODUCTION OF ETHANOL FROM ACETIC ACID

[75] Inventors: Ben W. Kiff, Lehigh Acres, Fla.; David J. Schreck, Cross Lanes, W. Va.

[73] Assignee: Union Carbide Corporation, Danbury, Conn.

[21] Appl. No.: 434,562

[22] Filed: Oct. 15, 1982

[51] Int. Cl.³ .................... C07C 31/08; C07C 29/136
[52] U.S. Cl. .................................................. 568/885
[58] Field of Search ....................................... 568/885

[56] References Cited

U.S. PATENT DOCUMENTS

| | | |
|---|---|---|
| 1,302,011 | 4/1919 | Christiansen . |
| 1,605,093 | 11/1926 | Bouvier et al. . |
| 1,971,742 | 8/1934 | Bertsch ............................ 260/156 |
| 2,091,800 | 8/1934 | Adkins et al. ..................... 260/156 |
| 2,440,678 | 5/1948 | Ford et al. ......................... 568/885 |
| 2,549,416 | 4/1951 | Brooks et al. ..................... 568/885 |
| 3,361,832 | 8/1963 | Pine et al. ......................... 260/638 |
| 4,113,662 | 9/1978 | Wall .................................. 252/473 |

*Primary Examiner*—J. E. Evans
*Attorney, Agent, or Firm*—Bernard Francis Crowe

[57] ABSTRACT

Ethanol is produced from acetic acid by esterifying the acetic acid with an olefin having at least 4 carbon atoms, hydrogenating the ester obtained into ethanol and a higher alcohol having at least 4 carbon atoms, removing the ethanol, dehydrating the higher alcohol back to the original olefin and recycling the olefin to esterify the acetic acid.

6 Claims, No Drawings

PRODUCTION OF ETHANOL FROM ACETIC ACID

BACKGROUND OF THE INVENTION

This invention pertains to the production of acetic acid and more particularly to a continuous cyclic process starting with acetic acid.

Ethanol is a very well-known chemical and has been produced as an industrial chemical for many years. A number of methods have been used for making ethanol, but only two are now employed on a large scale. One is the reaction of ethylene with water over a phosphoric acid catalyst. The phosphoric acid is supported on an inert support, such as, silica. This process is highly efficient and produces high quality ethanol. However, it suffers from the fact that ethylene is made from petroleum and natural gas liquids which are becoming scarce and progressively more expensive.

The other process involves the fermentation of carbohydrates to make ethanol. This is currently being used on a large scale and more plants are being built to make ethanol in this fashion. This method is practicable with the current low price of some agricultural products. However, it cannot be counted on for the long term because the raw materials are foodstuffs for animals and humans. With the prospective shortage of such materials for the next decade, fermentation cannot be counted on as the process of choice for the manufacture of very large quantities of industrial alcohol for the long run. This demand may be exacerbated if alcohol is to be used as a fuel for internal combustion engines as in gasohol.

It is therefore an object of this invention to provide an alternate source of ethanol.

It is another object of this invention to provide an alternate source of ethanol from cheap and readily available materials.

Other objects of this invention will become apparent to those upon the reading of the specification.

SUMMARY OF THE INVENTION

A method of producing ethanol has been discovered which comprises the following steps:

(1) contacting acetic acid with an olefinically unsaturated hydrocarbon having about 4 to about 10 carbon atoms, in the presence of a catalytic amount of an acidic esterification catalyst whereby an ester is obtained;

(2) hydrogenating the ester from step (1) whereby a mixture of ethanol and a higher alcohol containing the same number of carbons as the olefinically unsaturated hydrocarbon from step (1) is obtained;

(3) separating the mixture of step (2) by fractional distillation into ethanol and the higher alcohol;

(4) recovering the ethanol;

(5) dehydrating the higher alcohol into the original olefinically unsaturated hydrocarbon used in step (1); and (6) recycling the olefinically unsaturated hydrocarbon from step (5) with fresh acetic acid back to step (1) to repeat the process of esterification.

Acetic acid can be made from plentiful and relatively cheap starting materials in a variety of ways. For instance, one very efficient method is by the reaction of methanol with carbon monoxide in the liquid phase using a homogeneous rhodium catalyst. This process is in use in several very large plants and is commonly known as the Monsanto process. Since methanol can be produced from carbon monoxide and hydrogen made from coal or biomass, this may be considered making acetic acid from synthesis gas, the name usually given to a mixture of carbon monoxide and hydrogen. In this way, also, the ethanol made from this acetic acid may be considered to be synthesis gas based material.

Another source of acetic acid is from the liquid phase oxidation of butane. The intermediate alkanes, such as, butane are not as easily utilized as are the other portions of natural gas so their supply is predicted to be readily available at fairly moderate prices for a number of years to come.

The present invention is not limited to the use of acetic acid made by either of these two methods described above but can use acetic from any source.

There are several advantages to the method described above. Firstly, since acetic acid from any source can be used the production of ethanol is freed from dependence from any one source of raw material. Secondly, the ethanol produced is dry and therefore the refining step requires relatively small amounts of energy. In the previously used methods of making ethanol, i.e., the hydration of ethylene and the fermentation of carbohydrates, the most costly step is the separation of water from ethanol. Thirdly, the consumption of ethylenically unsaturated hydrocarbon is held to a very low level since it is recycled in the process. In fact, one can see that only mechanical losses would be responsible for the small amount of ethylenically unsaturated hydrocarbon lost. Lastly, the operations involved in this invention are all relatively simple and do not require complicated, costly and corrosion-resistant equipment.

Reaction of Acetic Acid with Olefins to Produce Esters

The addition of organic acids to the double bond of olefins to make esters is a well-known reaction. It is catalyzed by acidic materials and can be conducted as a liquid phase batch reaction. However, it is more conveniently carried out as a continuous operation in which the olefin and the acid are passed through a tubular reactor containing a solid acidic material. The solid acidic material may be any one of several types of compositions. Suitable materials include ion-exchange resins of the Dowex series supplied by Dow Chemical Company, the Amberlite series supplied by Rohm and Haas, the Amerlyst series also supplied by Rohm and Haas and similar compositions in which the cation has been replaced by hydrogen. Also, acidic synthetic zeolites manufactured by Union Carbide Corporation and Mobil Oil Corporation serve as catalysts under certain conditions.

Perfluorosulfonic acid resins which are copolymers of tetrafluoroethylene and a sulfonyl fluoride vinyl ether commercially available under the trademark Nafion from DuPont de Nemours Company of Wilmington, Delaware also can be used as catalyst. Suitable variations of these resins are described in U.S. Pat. No. 4,065,512 and in "DuPont Innovation", Volume 4, Number 3, Spring 1973. This material can be fabricated into a variety of forms, viz., pellets, rings, tubes, and the like and any one can be used to catalyze the esterification reaction. A preferred way to use the Nafion is to fill a tubular reactor with pellets, heat the apparatus to the desired temperature and simultaneously feed the acetic acid and olefin to the reactor. The ester, unreacted olefin and acid (if any) pass from the outlet to a distillation apparatus where the desired product is obtained in high purity.

In the practice of the instant invention it is preferred to use an olefin which will afford the following advantages:

(1) The olefin will react with the acetic acid cleanly and readily to form the ester.

(2) The alcohol corresponding to the olefin which is produced upon hydrogenation of the ester should have a boiling point high enough above that of ethanol so that the latter can be distilled away from said alcohol with no difficulty.

(3) The alcohol corresponding to the olefin should be one which is readily dehydrated to the olefin with ease in order that the olefin may be recycled to the first step in the process.

A number of olefins, i.e., ethylenically unsaturated hydrocarbons, which can be used in the instant invention include the following: 1-butene, 2-butene, isobutene, 1-amylene, 2-amylene, 3-amylene, iso-amylene, 1-hexene, 2-hexene, 3-hexene, 2-methyl-2-pentene, 3-methyl-2-pentene, 1-heptene, 1-octene, cyclohexene, and the like.

Hydrogenation of Ester to Ethanol Plus Another Alcohol

The hydrogenation of the ester in this reaction to make ethanol and another alcohol can be effected in a conventional liquid phase reaction in which a hydrogenation catalyst is mixed with the ester in a reaction vessel which will accommodate increased temperature and pressure. In such a reaction the liquid and catalyst mixture is heated to the desired temperature and hydrogen is admitted to raise the pressure to a specified level. As the reaction proceeds, additional hydrogen is fed to maintain a constant pressure. When no more hydrogen is consumed the reaction is terminated. The catalyst is filtered from the liquid (and retained for re-use) and the latter is distilled to isolate the ethanol from the reaction mixture. The co-formed alcohol is also recovered in the distillation and is fed to the dehydration apparatus to make olefin for recycling to the first step in the overall reaction.

It is preferred to conduct the hydrogenation in a continuous fashion in which the ester is vaporized and fed with hydrogen to contact the catalyst at the desired temperature and pressure. This reaction may be conducted in a back-mixed or recycled reactor or a tubular reactor. In this manner a substantial amount of the ester is converted per pass and it is not necessary to filter out the product to recover the catalyst.

The reaction temperatures and pressures for the hydrogenation can cover a rather wide range and are governed to a considerable extent by the nature and activity of the hydrogenation catalyst. Temperatures should not exceed about 300° C. and pressures should be less than about 5000 psig. When continuous operation is employed with a zinc-copper oxide catalyst, the reaction can be accomplished under much milder conditions. For instance, hydrogenation with such a catalyst can often be accomplished at 200° C. and 100 psig.

Any one of many hydrogenation catalysts can be used. Various combinations containing the oxide of copper in combination with the oxides of one or more other elements are effective. A particularly preferred composition is a reduced zinc oxide/copper oxide catalyst containing 65% of the former and 35% of the latter. Acidic catalysts must be avoided since they promote the dehydration of the alcohol derived from the olefin.

Dehydration of Olefin-Derived Alcohol

The alcohol co-produced with ethanol is converted back to the olefin by a conventional dehydration procedure. This can be accomplished as simply as heating the liquid alcohol in the liquid phase with an acid catalyst such as sulfuric acid, phosphoric acid, p-toluene sulfonic acid and the like. A preferred method is by continuous reaction in which the vapors of the alcohol are fed to a heated tubular reactor packed with a granular acidic or acid-reacting material. Examples of satisfactory materials to use as catalysts for this reaction are the perfluorosulfonic acid resin, Nafion, silica impregnated with phosphoric acid, boro-phosphoric acid, and the like. The reaction temperature should not exceed about 300° C. The dehydration is best conducted at atmospheric pressure or slightly above or below.

The dehydration product is the original olefin and water. The former is recycled to the original esterification zone and the latter is discarded.

Continuous Process For Making Ethanol From Acetic Acid

In the preceding sections the separate steps of the invention have been described as discreet operations. However, it can also be practiced as an integrated continuous reaction.

The invention is further described in the Examples which follow. All parts and percentages are by weight unless otherwise specified.

EXAMPLE 1

Preparation of Ester by Reaction of Olefin With Acetic Acid

A steel tube 60 cm long with a diameter of 2 cm was filed with granular Nafion 811 resin (obtained from the DuPont Corporation). The tube had a metal jacket 5 centimeters in diameter with inlet and outlet fittings through which liquid could be passed to regulate the reaction temperature.

Preliminary to the reaction, the Nafion was treated with dilute nitric acid to convert it to the acid form. It was then washed with distilled water to remove the acid and then with acetic acid to remove the water.

The pressure on the system was regulated to 15 psig and the tube temperature was adjusted to 50° C. by passing warm jacket water through the jacket. Acetic acid and 2-methyl-2-butene were then fed through the bottom of the tube at the rate of 1 mole of acid and 2 moles of olefin per hour. After the tube was filled, liquid overflowed continuously from the top. The product was collected and the unreacted 2-methyl-2-butene was distilled off at atmospheric pressure. The residue was substantially all tert-amyl acetate.

EXAMPLE 2

Hydrogenation of Ester

A back-mixed or recycled reactor (as described in Chemical Engineering Progress, May 1979, pp. 44–48) was charged with 30 grams of catalyst. Tert-amyl acetate was fed into the reactor at a rate of 40 ml per hour and hydrogen at a rate of 3.42 standard cubic feet per hour. The reaction is carried out at about 160° C. at a pressure of 4.22 kg/cm$^2$. A total of 600 ml of ester was fed over a 12-hour period. The product was collected and analyzed. A substantial portion of the ester had been hydrogenated to the corresponding alcohols. The material was distilled and ethanol and tert-amyl alcohol were separated from unreacted ester. The unreacted ester was recycled to the hydrogenation stage. Ethanol was collected for use and the tert-amyl alcohol was retained for feeding to the olefin regeneration step.

A catalyst used was reduced copper oxide/zinc oxide hydrogenation catalyst containing 35± weight percent CuO and 65± weight percent ZnO in pellet form about 0.6 cm in size. Reduction was conducted with hydrogen at 190° C. for 6 hours.

EXAMPLE 3

Dissociation of Alcohol Derived from Olefin

The reactor was a quartz tube 30 inches long and 1 inch in diameter enclosed in a hinged electric heater. The tube was packed with boro-phosphate on 4×8 mesh silica. This catalyst was made by heating 1 mole of boric acid and 1 mole of phosphoric acid until the mixture became molten. Granular silica was then added and the mass was stirred as it cooled so that the boro-phosphate became coated on the particles.

While the temperature of the tube was maintained at 150° C., tert-amyl alcohol was fed at the rate of 150 ml per hour. The effluent from the tube was cooled and analyzed. Decomposition of the tert-amyl alcohol to water and 2-butyl-2-butene was quantitative.

Although the invention has been described in its preferred forms with a certain amount of particularity, it is understood that the present disclosure of the preferred forms has been made only by way of example and that numerous changes may be resorted to without departing from the spirit and the scope of the invention.

We claim:

1. Method of producing ethanol from acetic acid which comprises the steps:

(1) contacting acetic acid with an olefinically unsaturated hydrocarbon having about 4 to about 10 carbon atoms, in the presence of a catalytic amount of an acidic esterification catalyst whereby an ester is obtained;

(2) hydrogenating the ester from step (1) whereby a mixture of ethanol and a higher alcohol containing the same number of carbons as the olefinically unsaturated hydrocarbon from step (1) is obtained;

(3) separating the mixture of step (2) by fractional distillation into ethanol and the higher boiling alcohol;

(4) recovering the ethanol;

(5) dehydrating the higher boiling alcohol into the original olefinically unsaturated hydrocarbon used in step (1); and (6) recycling the olefinically unsaturated hydrocarbon from step (5) with fresh acetic acid back to step (1) to repeat the process of esterification.

2. Method claimed in claim 1 wherein the olefinically unsaturated hydrocarbon is 2-methyl-2-butene.

3. Method claimed in claim 1 wherein the esterification catalyst is a perfluorosulfonic acid resin which is a copolymer of tetrafluoroethylene and a sulfonyl fluoride vinyl ether.

4. Method claimed in claim 1 wherein the hydrogenation is carried out over a reduced copper oxide/zinc oxide hydrogenation catalyst containing about 35± weight percent CuO and about 65 weight percent ZnO before reduction.

5. Method claimed in claim 1 wherein the dehydration of the higher alcohol into the original olefinically unsaturated hydrocarbon is carried out over a dehydration catalyst comprising equimolar amounts of molten boric acid and phosphoric acid.

6. Method claimed in claim 1 wherein the dehydration is carried out at a temperature of about 100° to about 200° C.

* * * * *